US007696235B2

(12) United States Patent
Woodward et al.

(10) Patent No.: US 7,696,235 B2
(45) Date of Patent: Apr. 13, 2010

(54) EP2 RECEPTOR AGONISTS FOR TREATING GLAUCOMA

(75) Inventors: David F. Woodward, Lake Forest, CA (US); June Chen, San Juan Capistrano, CA (US)

(73) Assignee: Allergan, Inc., Irvine, CA (US)

( * ) Notice: Subject to any disclaimer, the term of this patent is extended or adjusted under 35 U.S.C. 154(b) by 221 days.

(21) Appl. No.: 11/472,145

(22) Filed: Jun. 21, 2006

(65) Prior Publication Data

US 2007/0049625 A1    Mar. 1, 2007

Related U.S. Application Data

(60) Provisional application No. 60/712,586, filed on Aug. 29, 2005.

(51) Int. Cl.
*A61K 31/44*     (2006.01)
*C07D 213/62*    (2006.01)
(52) U.S. Cl. .................... 514/347; 514/340; 546/268.4; 546/293
(58) Field of Classification Search ........................ None
See application file for complete search history.

(56) References Cited

U.S. PATENT DOCUMENTS

2005/0065133 A1    3/2005   Lee et al.

FOREIGN PATENT DOCUMENTS

| EP | 1205189 | * | 5/2002 |
| WO | WO99/19300 | | 4/1999 |
| WO | WO2004/078169 | | 9/2004 |

OTHER PUBLICATIONS

Cioffi G A; Van Buskirk E M Microvasculature of the anterior optic nerve. Survey of ophthalmology (1994), 38 Suppl S107-16; discussion S116-7. Journal code: 0404551. ISSN:0039-6257. PubMed ID 7940132 AN 95026416 Medline.
Matsui M Ophthalmological aspects of systemic vasculitis. Nippon rinsho. Japanese journal of clinical medicine (1994), 52(8), 2158-63. Journal code: 0420546. ISSN:0047-1852. PubMed ID 7933604 AN 95019194 Medline.
Schwartz B Circulatory defects of the optic disk and retina in ocular hypertension and high pressure open-angle glaucoma. Survey of ophthalmology (1994), 38 Suppl S23-34. Journal code: 0404551. ISSN:0039-6257. PubMed ID 7940145 AN 95026429 Medline.
Starr, Michael S.. Further studies on the effect of prostaglandin on intraocular pressure in the rabbit. Experimental Eye Research (1971), 11(2), 170-7. CODEN: EXERA6 ISSN:0014-4835. CAN 75:15707 AN 1971:415707 CAPLUS.
Bito, Laszlo Z.. Prostaglandins , other eicosanoids, and their derivatives as potential antiglaucoma agents. Glaucoma: Appl. Pharmacol. Med. Treat., [Proc. Meet.] (1984), Meeting Date 1983, 477-505. CODEN: 53PRA8 CAN 102:198122 AN 1985:198122 Caplus.
Paralkar et al, An EP2 receptor-selective prostaglandin $E_2$ agonist induces bone healing, Proc. Nat. Acad. Sci., vol. 100, No. 11, pp. 6736-6740, 2003.

* cited by examiner

*Primary Examiner*—Zinna N Davis
(74) *Attorney, Agent, or Firm*—Kevin J. Forrestal; John E. Wurst; Allergan, Inc.

(57) ABSTRACT

The present invention relates to novel EP2 Receptor agonists that are useful for treating glaucoma and other conditions and indications in man. Ocular hypotensive agents are useful in the treatment of a number of various ocular hypertensive conditions, such as post-surgical and post-laser trabeculectomy ocular hypertensive episodes, glaucoma, and as presurgical adjuncts.

4 Claims, 8 Drawing Sheets

FIGURE 1

Effect of 0.1% (3-{[(4-tert-butyl-benzyl)-(pyridine-3-sulfonyl)-amino]-methyl}-phenoxy)-acetic acid on Dog Intraocular Pressure
5 Day Once Daily Dosing, Topical, n = 8

Effect of 0.1% Isopropyl Ester of (3-{[(4-tert-butyl-benzyl)-(pyridine-3-sulfonyl)-amino]-methyl}-phenoxy)-acetic acid on Monkey Intraocular Pressure One Day Single Dose, Topical, n = 9

EP2 RECEPTOR AGONISTS FOR TREATING GLAUCOMA

CROSS REFERENCE TO RELATED APPLICATIONS

This application is based on, and claims the benefit of, U.S. Provisional Application No. 60/712,586, filed Aug. 29, 2005, and which is incorporated herein by reference.

BACKGROUND OF THE INVENTION

1. Field of the Invention

The present invention relates to novel EP2 Receptor agonists that are useful for treating glaucoma and other conditions and indications in man.

2. Description of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

It has long been known that one of the sequelae of glaucoma is damage to the optic nerve head. This damage, referred to as "cupping", results in depressions in areas of the nerve fiber of the optic disk. Loss of sight from this cupping is progressive and can lead to blindness if the condition is not treated effectively.

Unfortunately lowering intraocular pressure by administration of drugs or by surgery to facilitate outflow of the aqueous humor is not always effective in obviating damage to the nerves in glaucomatous conditions. This apparent contradiction is addressed by Cioffi and Van Buskirk [*Surv. of Ophthalmol.*, 38, Suppl. p. S107-16, discussion S116-17, May 1994] in the article, "Microvasculature of the Anterior Optic Nerve". The abstract states:

The traditional definition of glaucoma as a disorder of increased intraocular pressure (IOP) oversimplifies the clinical situation. Some glaucoma patients never have higher than normal IOP and others continue to develop optic nerve damage despite maximal lowering of IOP. Another possible factor in the etiology of glaucoma may be regulation of the regional microvasculature of the anterior optic nerve. One reason to believe that microvascular factors are important is that many microvascular diseases are associated with glaucomatous optic neuropathy.

Subsequent to Cioffi, et al., Matusi published a paper on the "Ophthalmologic aspects of Systemic Vasculitis" [*Nippon Rinsho*, 52 (8), p. 2158-63, August 1994] and added further support to the assertion that many microvascular diseases are associated with glaucomatous optic neuropathy. The summary states:

Ocular findings of systemic vasculitis, such as polyarteritis nodosa, giant cell angitis and aortitis syndrome were reviewed. Systemic lupus erythematosus is not categorized as systemic vasculitis, however its ocular findings are microangiopathic. Therefore, review of its ocular findings was included in this paper. The most common fundus finding in these diseases is ischemic optic neuropathy or retinal vascular occlusions. Therefore several points in diagnosis or pathogenesis of optic neuropathy and retinal and choroidal vaso-occlusion were discussed. Choroidal ischemia was able to be diagnosed clinically, since fluorescein angiography was applied in these lesions. When choroidal arteries are occluded, overlying retinal pigment epithelium is damaged. This causes disruption of barrier function of the epithelium and allows fluid from choroidal vasculatures to pass into subsensory retinal spaces. This is a pathogenesis of serous detachment of the retina. The retinal arterial occlusion resulted in non-perfused retina. Such hypoxic retina released angiogenesis factors which stimulate retinal and iris neovascularizations and iris neovascularizations may cause neovascular glaucoma.

B. Schwartz, in "Circulatory Defects of the Optic Disk and Retina in Ocular Hypertension and High Pressure Open-Angle Glaucoma" [*Surv. Ophthalmol.*, 38, Suppl. pp. S23-24, May 1994] discusses the measurement of progressive defects in the optic nerve and retina associated with the progression of glaucoma. He states:

Fluorescein defects are significantly correlated with visual field loss and retinal nerve fiber layer loss. The second circulatory defect is a decrease of flow of fluorescein in the retinal vessels, especially the retinal veins, so that the greater the age, diastolic blood pressure, ocular pressure and visual field loss, the less the flow. Both the optic disk and retinal circulation defects occur in untreated ocular hypertensive eyes. These observations indicate that circulatory defects in the optic disk and retina occur in ocular hypertension and open-angle glaucoma and increase with the progression of the disease.

Thus, it is evident that there is an unmet need for agents that have neuroprotective effects in the eye that can stop or retard the progressive damage that occurs to the nerves as a result of glaucoma or other ocular afflictions.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.* 1971, 11, pp. 170-177; Bito, L. Z. *Biological Protection with Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

Certain $EP_2$-receptor-selective prostaglandin $E_2$ agonists are disclosed in Paralkar V M et al. Proc. Nat. Acad. Sci. vol 100 pp 6736-6740, 2003.

BRIEF SUMMARY OF THE INVENTION

The present invention provides a method of treating ocular hypertension or lowering elevated intraocular pressure (IOP) by administering to a mammal having ocular hypertension a therapeutically effective amount of N,N' dibenzyl pyridyl sulfonamide compound having $EP_2$ receptor agonist activity which compound may be represented by the formula wherein R is hydrogen or an aliphatic straight chain or branched radical comprised of 1 to 20 carbon atoms, or R is a polar esterifying group which may be represented by the formula $(CHR^1CYHX)_nH$ wherein X is O or S; Y is selected from the group consisting of H, —OH, —COOH, $CONH_2$, $SO_3H$ and $PO_3H_2$ and n is an integer of from 1 to 10, or R is selected from the group consisting of (i) acyl sulfonamide radicals represented by the formula (i) Sulfonamides radicals represented by the formula $SO_2NR^1_2$ and (iii)

wherein $R^1$ is selected from the group consisting of hydrogen and alkyl radicals comprised of from 1 to 20 carbon atoms.

In a further aspect, the present invention relates to an ophthalmic solution comprising a therapeutically effective amount of a compound of the above formula or a pharmaceutically-acceptable salt thereof, in admixture with a non-toxic, ophthalmically acceptable liquid vehicle, packaged in a container suitable for metered application.

In a still further aspect, the present invention relates to a pharmaceutical product, comprising
 a container adapted to dispense its contents in a metered form; and
 an ophthalmic solution therein, as hereinabove defined.

Finally, certain of the compounds represented by the above formula, disclosed below and utilized in the method of the present invention are novel and unobvious.

DETAILED DESCRIPTION OF THE INVENTION

The present invention relates to the use of N,N'dibenzyl pyridyl sulfonamides having $EP_2$-receptor agonist activity for treating ocular hypertension in and/or providing neuroprotection to a mammal, e.g. a human, in need of such treatment. The compounds used in accordance with the present invention are encompassed by the following structural formula:

wherein R is an aliphatic straight chain or branched radical comprised of from 1 to 20 carbon atoms, or R is a polar esterifying group which may be represented by the formula $(CHR^1CYHX)_nH$ wherein X is O or S; Y is selected from the group consisting of H, —OH, —COOH, CONH$_2$, SO$_3$H and PO$_3$H$_2$ and n is an integer of from 1 to 10, or R is selected from the group consisting of (i) acyl sulfonamide radicals represented by the formula (ii) Sulfonamide radicals represented by the formula and (iii)

wherein R$^1$ is selected from the group consisting of hydrogen and alkyl radicals comprised of from 1 to 20 carbon atoms, and pharmaceutically-acceptable salts thereof.

Preferably, R is a lower alkyl radical, i.e. a C$_1$ to C$_7$ alkyl, e.g. a C$_1$ to C$_4$ alkyl radical such as methyl, ethyl, isopropyl, isobutyl, etc. More preferably, R is a methyl or ethyl or isopropyl radical, e.g. a methyl or isopropyl radical. Most preferably R is a isopropyl radical.

Preferably R$^1$ is H or a lower alkyl radical, i.e. a C$_1$ to C$_7$ alkyl, e.g. a C$_1$ to C$_4$ alkyl radical such as methyl, ethyl, isopropyl, isobutyl, etc. More preferably, R is a methyl or ethyl or isopropyl radical, e.g. a methyl or isopropyl radical. Most preferably R is a isopropyl radical.

Preferably X is O.

Preferably Y is hydrogen.

When R is a polar esterifying group it may be (CH$_2$CH$_2$O)$_n$H, e.g. C$_2$H$_4$OH.

The following compounds may be used in the method of the present invention.

(3-{[(4-tert-butyl-benzyl)-(pyridine-3-sulfonyl)-amino]-methyl}-phenoxy)-acetic acid;
(3-{[(4-tert-butyl-benzyl)-(pyridine-3-sulfonyl)-amino]-methyl}-phenoxy)-acetic acid; isopropyl ester
(3-{[(4-tert-butyl-benzyl)-(pyridine-3-sulfonyl)-amino]-methyl}-phenoxy)-acetic acid; n-butyl ester
(3-{[(4-tert-butyl-benzyl)-(pyridine-3-sulfonyl)-amino]-methyl}-phenoxy)-acetic acid; methyl ester
(3-{[(4-tert-butyl-benzyl)-(pyridine-3-sulfonyl)-amino]-methyl}-phenoxy)-acetic acid; 2-hydroxy ethyloxyethyl
(3-{[(4-tert-butyl-benzyl)-(pyridine-3-sulfonyl)-amino]-methyl}-phenoxy)-acetic acid; 2-hydroxy propyl and the pharmaceutically-acceptable salts of said compounds.

A pharmaceutically-acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions including the above compounds may be prepared by combining a therapeutically effective amount of at least one compound according to the present invention, or a pharmaceutically-acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically-acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-8.0 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations for use in the method of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

The invention is further illustrated by the following examples which are illustrative of a specific mode of practicing the invention and are not intended as limiting the scope of the claims.

Example 1

Measurement of intraocular pressure studies in dogs involved applanation pneumatonometry performed in Beagle dogs of both sexes. The animals remained conscious throughout the study and were gently restrained by hand. The drug was administered topically to one eye using a dropper bottle to deliver approximately a 35 µl volume, the other eye received vehicle (1% polysorbate 80 in 5 mM Tris HCl) as a control. Proparacaine at 0.25% was used for corneal anesthesia during tonometry. Intraocular pressure was determined just before drug administration and at 2, 4, 6 hours thereafter on each day of the 5 day study. Measurement of ocular surface hyperemia was performed immediately before each of the intraocular pressure readings. Ocular surface hyperemia grading was semi-quantitative and assessed according to a 5 point scoring scale used for clinical evaluations: 0=none; 0.5=trace; 1=mild; 2=moderate; and 3=severe.

Cynomolgus monkeys (*Macaca fascicularis*) were used for the intraocular pressure studies. Each animal was unilaterally laser-treated by circumferential laser photocoagulation to induce ocular hypertension in one eye. Conscious female animals were trained sit in custom design chairs and to accept applanation pneumatonometry. The drug was administered topically to one eye using a dropper bottle to deliver approximately a 35 µl volume, the other eye received vehicle (1% polysorbate 80 in 5 mM Tris HCl) as a control. Proparacaine at 0.25% was used for corneal anesthesia during tonometry. Intraocular pressure was determined just before drug administration and at 2, 4, 6, and 24 hours.

The results of these experiments are reported in FIGS. 1 through 8.

Figure 1:
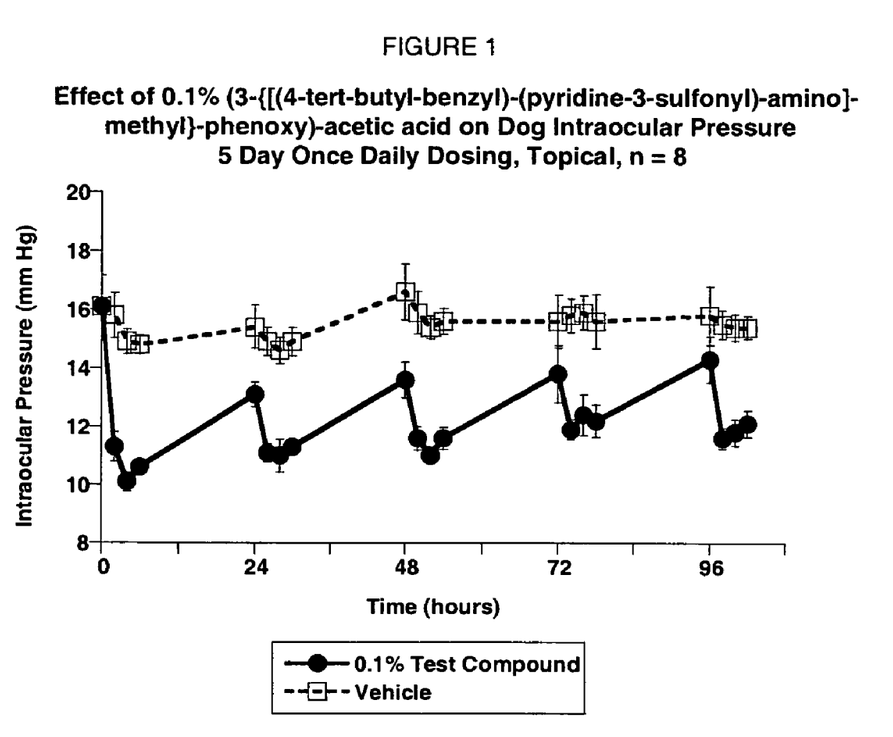
FIG. 1 shows the effect on the IOP of dogs by the administration of a compound of the invention.
Figure 2:
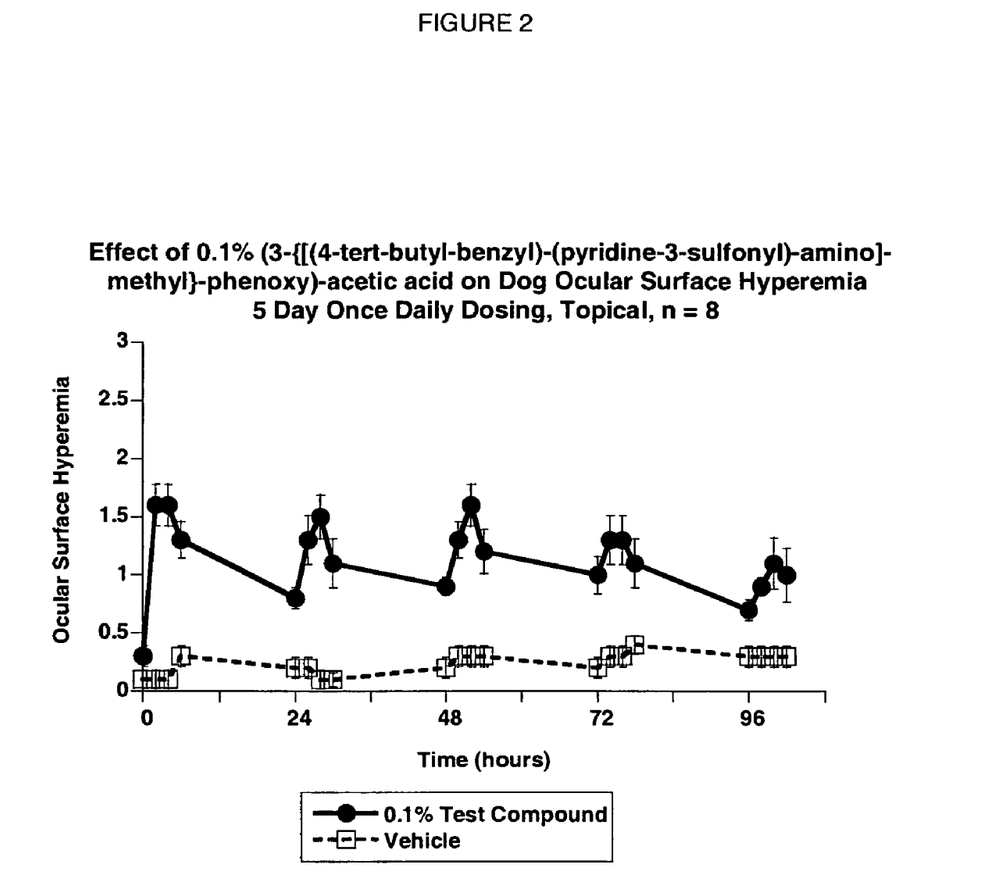
FIG. 2 shows the effect on the ocular surface hyperemia of dogs by the administration of a compound of the invention.

FIGS. 1 and 2 show that a single daily dose of (3-{[(4-tert-butyl-benzyl)-(pyridine-3-sulfonyl)-amino]-methyl}-phenoxy)-acetic acid over a 5 day period is effective for reducing IOP of the dogs with mild ocular surface hyperemia that diminishes over time.

Figure 3:
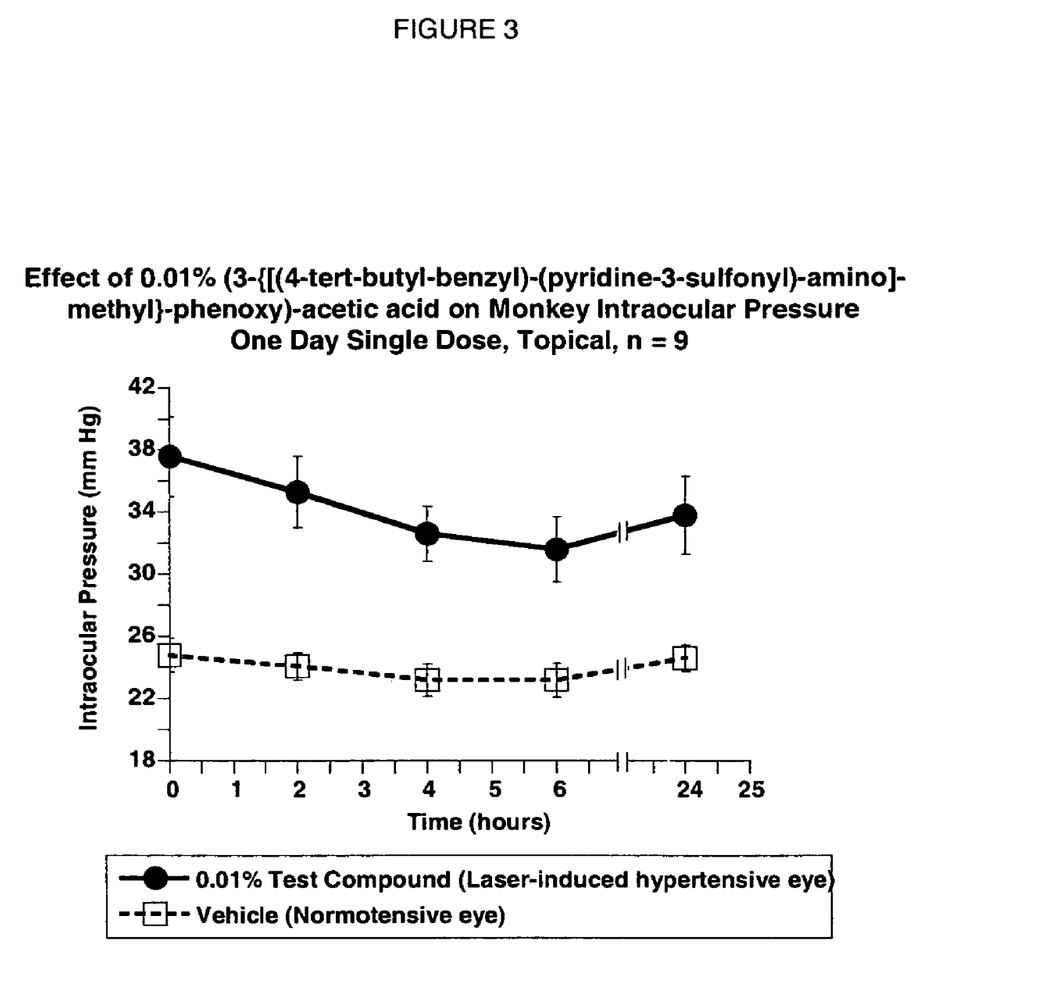
FIG. 3 shows the effect on the IOP of monkeys by the administration of a solution comprising 0.01% w/v of a compound of the invention.
Figure 4:
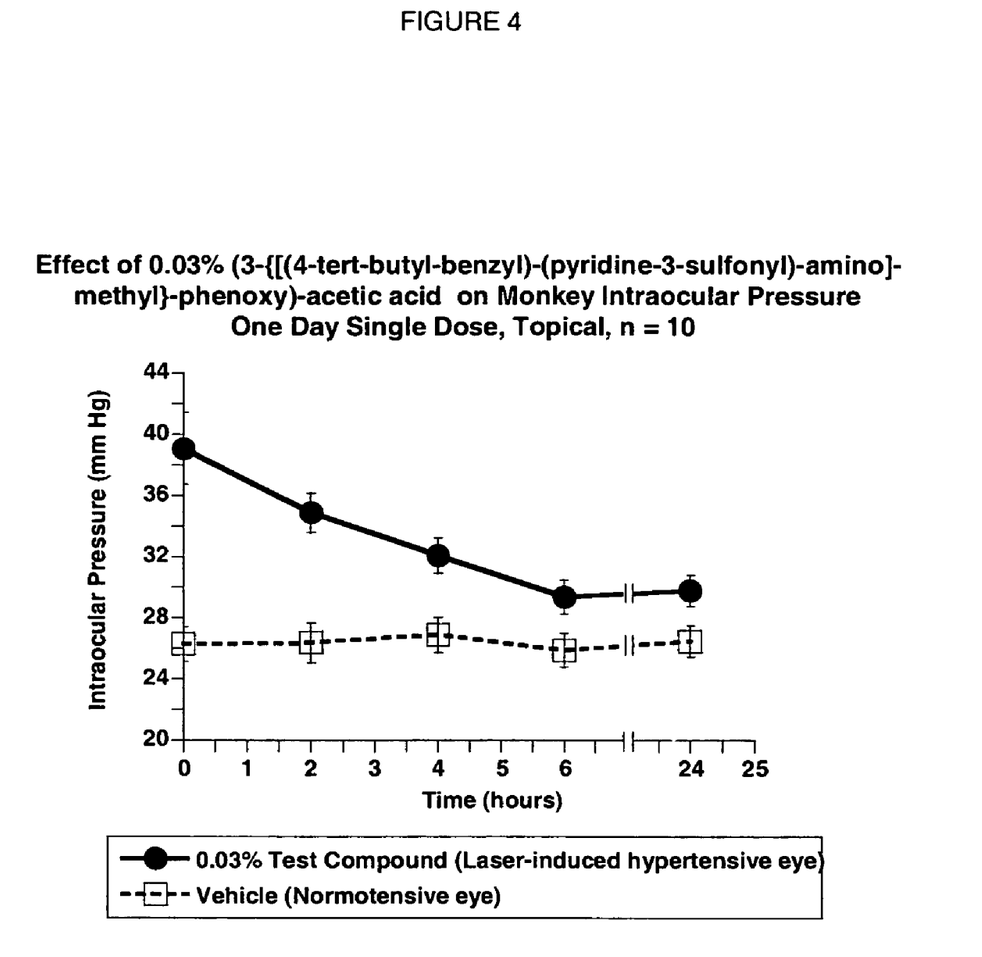
FIG. 4 shows the effect on the IOP of monkeys by the administration of a solution comprising 0.03% w/v of a compound of the invention.
Figure 5:
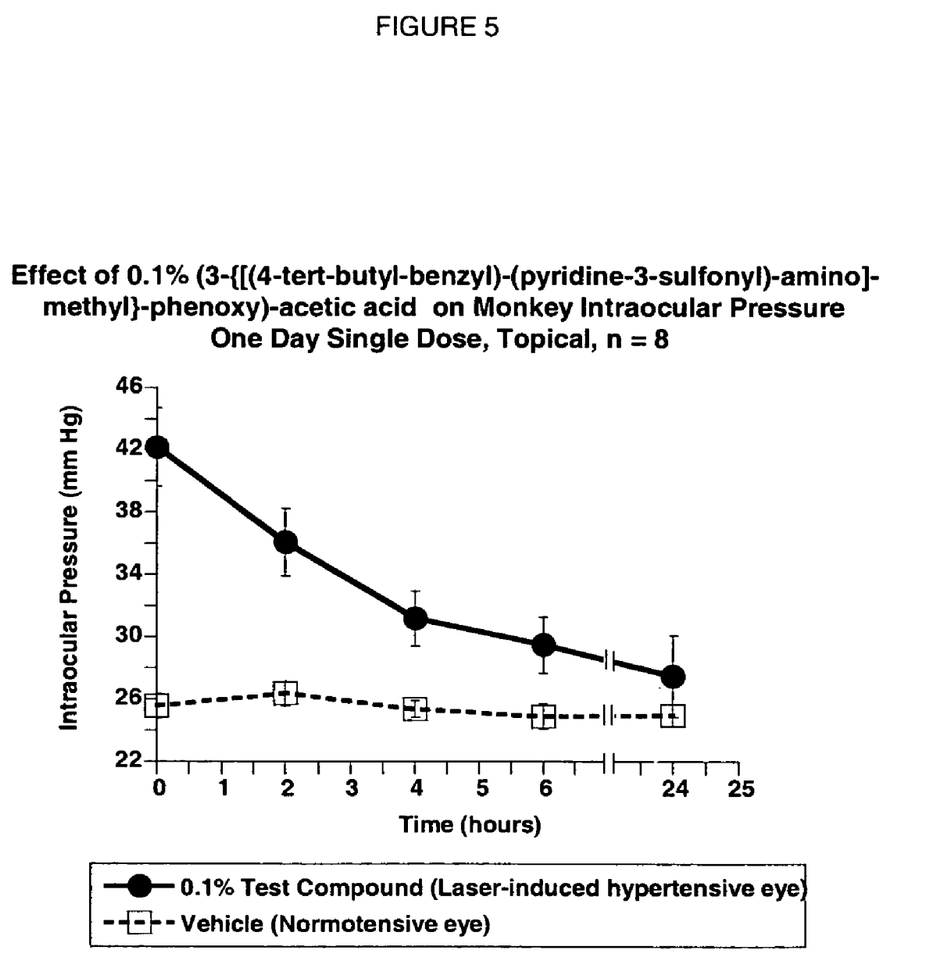
FIG. 5 shows the effect on the IOP of monkeys by the administration of a solution comprising 0.1% w/v of a compound of the invention.

FIGS. 3 through 5 show that a single dose of 0.01%, 0.03% or 0.1% (3-{[(4-tert-butyl-benzyl)-(pyridine-3-sulfonyl)-amino]-methyl}-phenoxy)-acetic acid to the eye of a monkey lowers the elevated IOP over 24 hours, almost to the level of the control normotensive eye for the two higher doses.

Figure 6:
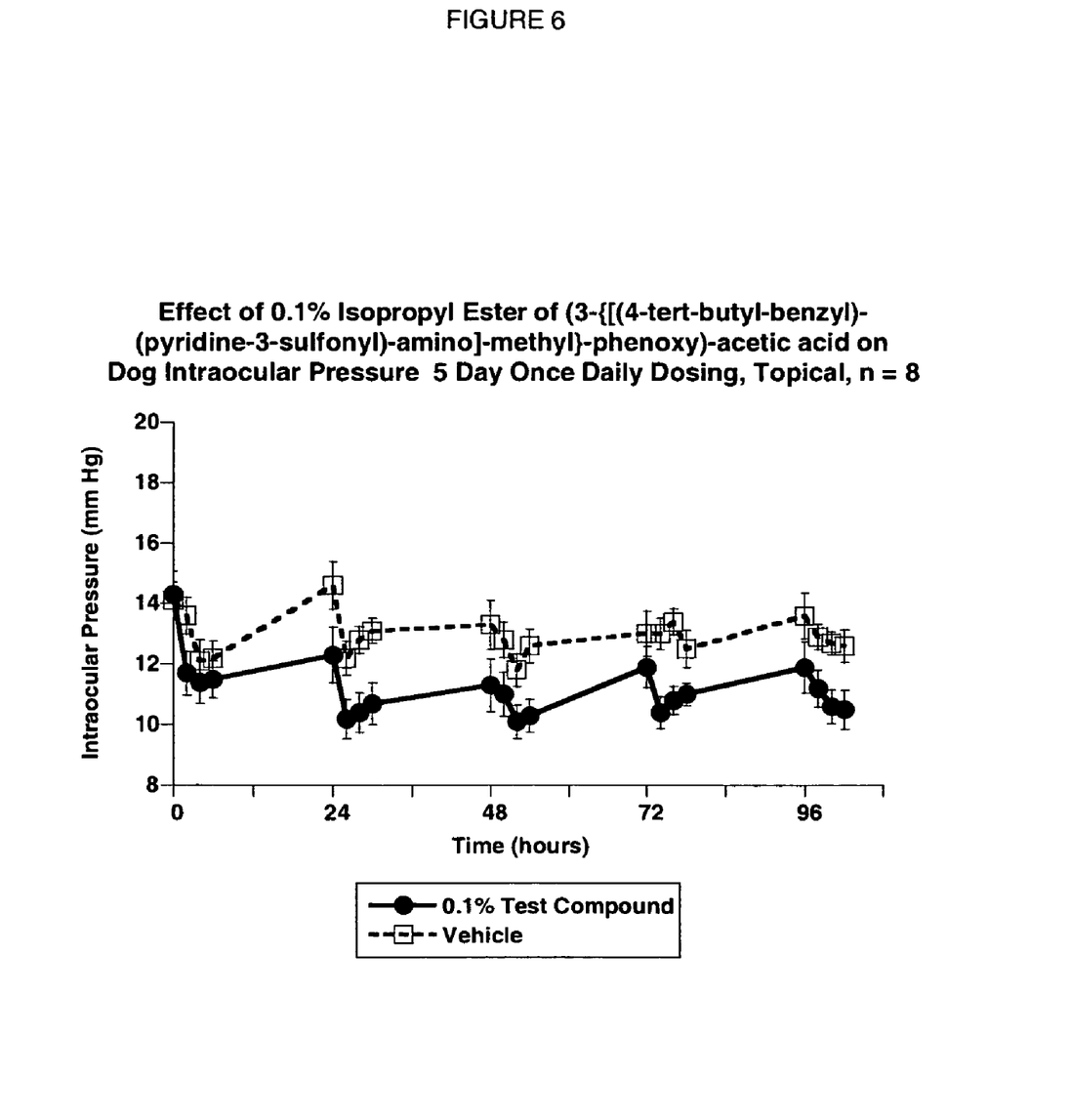
FIG. 6 shows the effect on the IOP of dogs by the administration of a compound, as an isopropyl ester, of the invention.
Figure 7:
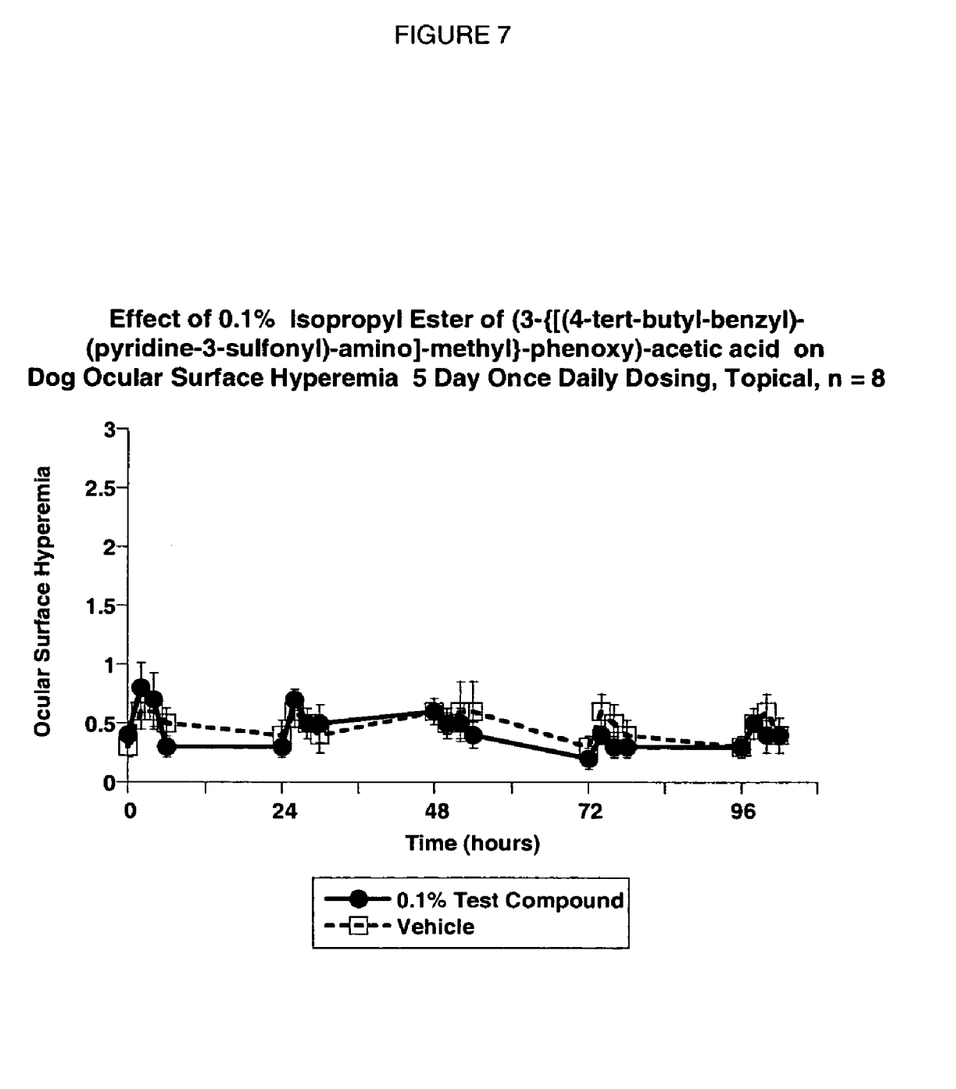
FIG. 7 shows the effect on the ocular surface hyperemia of dogs by the administration of a compound, as an isopropyl ester, of the invention.

FIGS. 6 and 7 show that a single dose of the isopropyl ester of (3-{[(4-tert-butyl-benzyl)-(pyridine-3-sulfonyl)-amino]-methyl}-phenoxy)-acetic acid over a 5 day period is effective for reducing IOP of the dogs with minimal ocular surface hyperemia.

Figure 8:
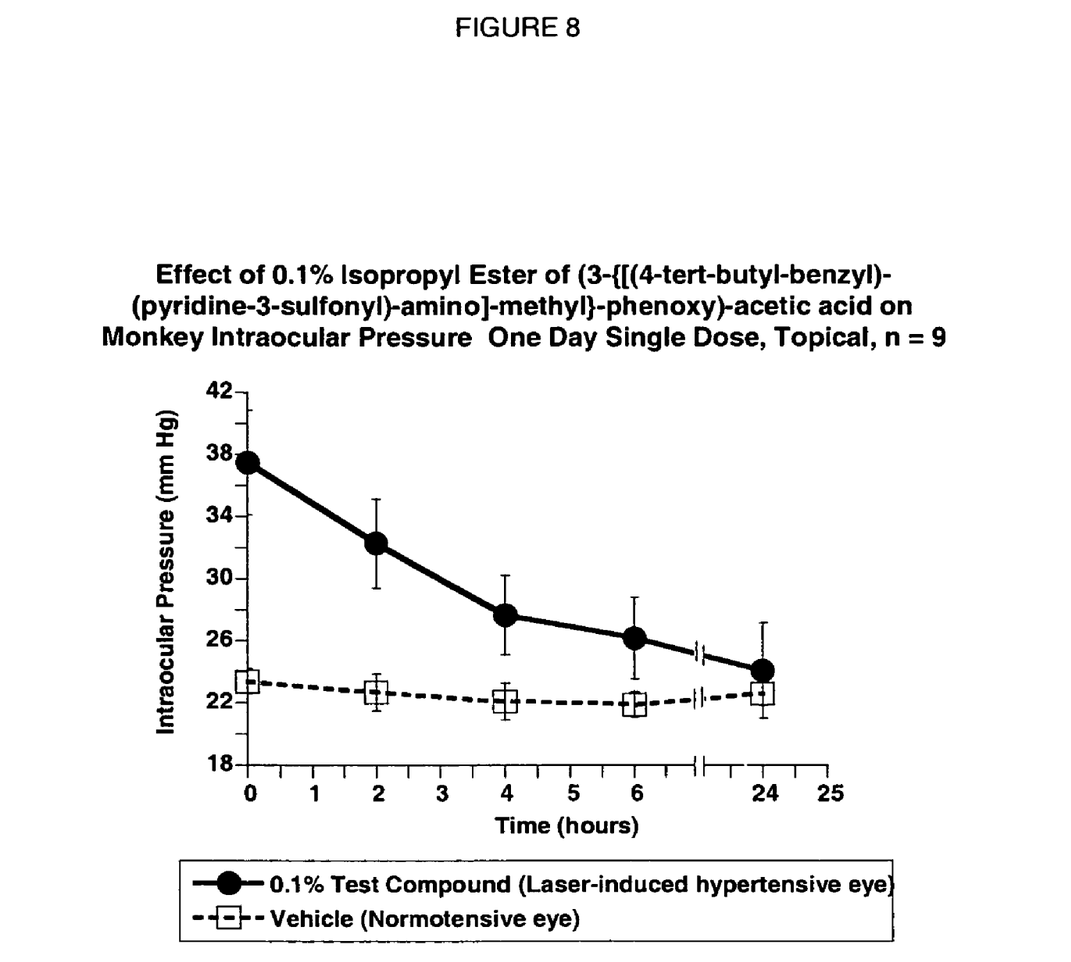
FIG. 8 shows the effect on the IOP of monkeys by the administration of a solution comprising 0.1% w/v of a compound, as an isopropyl ester, of the invention.

FIG. 8 shows that a single dose of the isopropyl ester of (3-{[(4-tert-butyl-benzyl)-(pyridine-3-sulfonyl)-amino]-methyl}-phenoxy)-acetic acid to the eye of a monkey lowers the elevated IOP over 24 hours almost to the level of the control normotensive eye.

While particular embodiments of the invention have been described it will be understood of course that the invention is not limited thereto since many obvious modifications can be made and it is intended to include within this invention any such modifications as will fall within the scope of the appended claims. For example, the present invention may utilize any other N,N' dibenzyl pyridyl sulfonamide compound having EP$_2$ receptor agonist activity in addition to the compounds represented by the above general formula to treat ocular hypertension or provide neuroprotection to the eyes of a mammal, e.g. a human.

The invention claimed is:

1. A compound represented by the following formula:

wherein R is methyl, ethyl, propyl, isopropyl, n-butyl, isobutyl, pentyl, hexyl, heptyl, octyl, nonyl, or decyl, or R is a polar esterifying group which may be represented by the formula $(CHR^1CHYX)_nH$ wherein X is O or S; Y is selected from the group consisting of H,
—OH, —COOH, CONH$_2$, SO$_3$H and PO$_3$H$_2$ and n is an integer of from 1 to 10, or R is selected from the group consisting of
  (i) acyl sulfonamide radicals represented by the formula (ii) Sulfonamide radicals represented by the formula and
  (iii)

wherein R$^1$ is independently selected from the group consisting of hydrogen and alkyl radicals comprised of from 1 to 20 carbon atoms and pharmaceutically-acceptable salts thereof.

2. The compound of claim 1 wherein R is isopropyl or isobutyl.

3. The compound of claim 1 wherein R is a polar esterifying group represented by the formula $(CHR^1CHYX)_nH$ wherein X is O or S; Y is selected from the group consisting of H, —OH, —COOH, CONH$_2$, SO$_3$H and PO$_3$H$_2$ and n is an integer of from 1 to 10.

4. The compound of claim 3 wherein X is O, Y is hydrogen and R$^1$ is H.

* * * * *

UNITED STATES PATENT AND TRADEMARK OFFICE
CERTIFICATE OF CORRECTION

PATENT NO. : 7,696,235 B2  Page 1 of 1
APPLICATION NO. : 11/472145
DATED : April 13, 2010
INVENTOR(S) : David F. Woodward et al.

It is certified that error appears in the above-identified patent and that said Letters Patent is hereby corrected as shown below:

In column 2, line 23, delete "angitis" and insert -- angiitis --, therefor.

In column 3, line 54, delete "(i)" and insert -- (ii) --, therefor.

Signed and Sealed this

Sixteenth Day of November, 2010

David J. Kappos
*Director of the United States Patent and Trademark Office*